Dec. 19, 1950 H. M. EDDIE Plant Pat. 1,000
ROSE PLANT
Filed Feb. 14, 1950
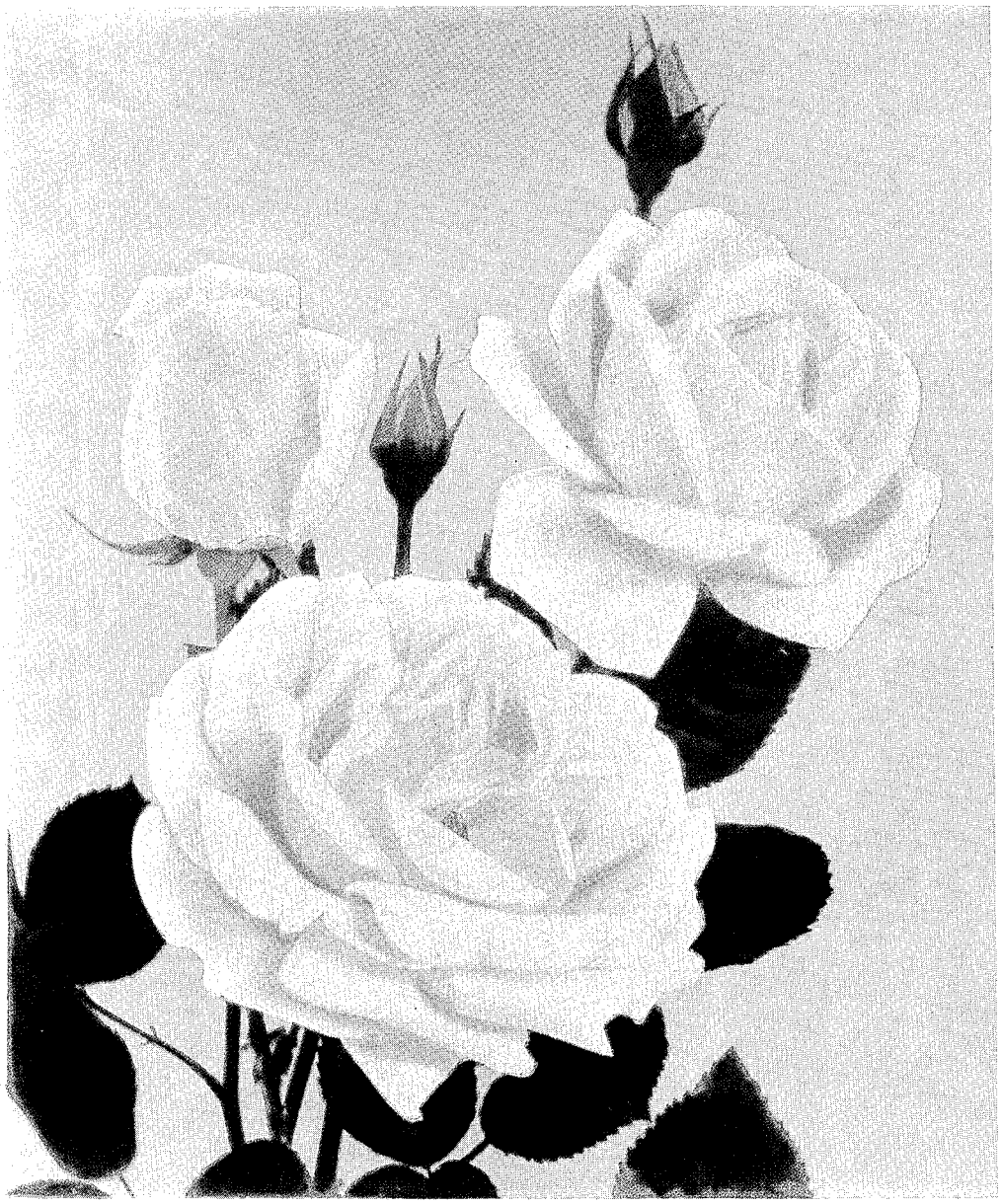
Inventor.
H. M. Eddie
By Robert Cobb
Attorneys Patented Dec. 19, 1950

Plant Pat. 1000

UNITED STATES PATENT OFFICE 1,000

ROSE PLANT

Henry Matheson Eddie, Vancouver, British Columbia, Canada, assignor to H. M. Eddie & Sons, Ltd., Vancouver, British Columbia, Canada, a corporation of British Columbia Application February 14, 1950, Serial No. 144,074

1 Claim. (Cl. 47—61)

This invention relates to a new and distinct variety of hybrid tea rose plant, originated by crossing the variety "Royal Visit" (unpatented) and the variety "Cynthia Brooke" (Plant Patent No. 551).

The new variety is entirely distinguishable from either of its parents, not only as to the coloring of the flowers, but also in other important characteristics, and resulting in a novel and unusual combination of characteristics heretofore unknown in rose varieties of the hybrid tea class.

Among the dominant distinctions are:

(1) The basic color of the full open blooms of the variety is capucine buff, while the backs of the petals are a warmer shade of capucine orange.

(2) The plant is exceedingly vigorous in growth and produces a great abundance of large, well-formed flowers throughout the entire blooming season.

(3) The foliage is also produced in abundance and is a glossy, dark green color and is extraordinarily resistant to disease.

This new variety most nearly resembles its seed parent "Royal Visit," but differs therefrom in the following respects: (1) It is nearly twice as strong a grower; (2) has longer, darker green and glossier foliage; (3) the peduncle is stronger and heavier; (4) the texture of the petals is heavier; and (5) the flowers are larger and of a softer shade of color.

Asexual reproduction of this new variety by budding at Vancouver, British Columbia, shows that the foregoing characteristics come true to form and are established and transmitted through succeeding propagations.

In the drawing are shown specimens of the flowers and foliage of the new variety in various stages of development.

The following is a detailed description of the new variety, with the color terminology in accordance with Ridgway's Color Standards and Nomenclature and ordinary dictionary meaning.

Observations were made in the field outdoors at Vancouver, B. C., during the month of September.

Class: Hybrid tea.

Parentage: Seedling.

*Seed parent.*—"Royal Visit."

*Pollen parent.*—"Cynthia Brooke."

*Flower*

Bud:

*Size.*—When beginning to open, bud is approximately 2 inches long, 1¾ inches wide at base.

*Shape.*—Wide at base, tapering slightly to wide point.

*Color.*—Salmon Orange, Plate II; Buff Yellow at base, Plate IV. Tight bud color is Bitter Orange, Plate II.

*Calyx.*—Five sepals of light Oriental Green, Plate XVIII; back of calyx slightly deeper shade of green.

*Peduncle.*—Very heavy and stiff. Color—Biscay Green, Plate XVII, with bronzy trace throughout.

*Opening.*—Slow to perfect flowers with low percentage with confused center.

Bloom:

*Size.*—Large; often 7 inches.

*Form.*—High-centered, wide-petalled, semi-globular; petals tightly compacted, recurving at edges.

*Color.*—Full open flower is Capucine Buff, Plate III. Backs of petals—warm shade of Capucine Orange, Plate III.

*Quantity.*—Flowers produced in great abundance throughout whole season, from June to October.

*Fragrance.*—Slightly aromatic.

*Longevity.*—From opening bud, the flower will remain attractive 6–7 days.

Petals:

*Shape.*—Broader than long.

*Size.*—Outer petals approximately 5½ x 3 inches.

*Texture.*—Very heavy.

*Color.*—Capucine Buff, Plate III. Base of petals Buff Yellow, Plate III.

*Appearance.*—Satiny on upper side, smooth on under side.

Reproductive organs: Pistils bunched on long styles; stamens golden yellow, interspersed with inner petals.

Fruit: Flattened round, with adherent calyx.

*Plant*

Growth:

*Form.* — Vigorous upright bush which branches freely.

*Vigor.*—Very sturdy and strong.

*Disease resistance.*—Practically immune to mildew and other common diseases.

*Blooming habit.*—Buds open slowly into large flowers of perfect form with small percentage with confused centers.

Foliage:

*Leaflets.*—Five.

*Quantity.*—Abundant.

*Size.*—Leaves 6–7 inches long. Terminal leaflets—3½ to 4½ inches long, 2½ to 3 inches wide.

*Shape.*—Broadly ovate with sharp apex.

*Edge.*—Medium serration.

*Color.*—Front of leaves—Deep Cerro Green, Plate V. Back of leaves—Lettuce Green, Plate V.

*Substance.*—Very heavy.

*Rachis or midrib.*—Heavy; grooved on upper side; six to seven thorns on under side.

*Stipules.*—None.

Stems:

*Strength.*—Very vigorous.

*Internodes.*—Short.

*Color.*—Biscay Green, Plate XVIII; rich brown on sunny side.

*Thorns.*—Quantity—average; narrow with slight hook. Color—light reddish brown.

I claim:

A new and distinct variety of hybrid tea rose plant, characterized as to novelty by its vigorous growth, its extraordinary resistance to disease, its abundant, large dark green, glossy foliage, its strong peduncle, its large, high-centered, long-lasting well-formed flowers which are basically capucine buff in color and composed of heavy-textured, satiny petals, and by the great abundance of flowers produced throughout the blooming season, substantially as shown and described.

HENRY MATHESON EDDIE.

No references cited.